United States Patent [19]

Shofner et al.

[11] Patent Number: 5,469,253

[45] Date of Patent: Nov. 21, 1995

[54] APPARATUS AND METHOD FOR TESTING MULTIPLE CHARACTERISTICS OF SINGLE TEXTILE SAMPLE WITH AUTOMATIC FEED

[75] Inventors: Frederick M. Shofner; Youe-T Chu; Joseph C. Baldwin; Michael E. Galyon; Benjamin M. Kacenas, all of Knoxville; Gordon F. Williams, Norris, all of Tenn.

[73] Assignee: Zellweger Uster, Inc., Knoxville, Tenn.

[21] Appl. No.: 962,898

[22] Filed: Oct. 16, 1992

Related U.S. Application Data

[63] Continuation-in-part of Ser. No. 493,961, Mar. 14, 1990, Pat. No. 5,270,787.

[51] Int. Cl.[6] .......................... G01N 21/00; G01N 15/14; G01L 5/04
[52] U.S. Cl. .......................... 356/238; 73/160; 356/383; 356/385
[58] Field of Search .......................... 356/238, 383–387, 356/430; 19/0.23, 0.25, 300; 250/560; 73/160

[56] References Cited

U.S. PATENT DOCUMENTS

| | | | |
|---|---|---|---|
| 3,069,964 | 12/1962 | Simon | 356/385 |
| 3,816,001 | 6/1974 | Duncan et al. | |
| 3,936,665 | 2/1976 | Donoghue | 364/563 |
| 4,027,162 | 5/1977 | Knollenberg | 250/345 |
| 4,511,253 | 4/1985 | Glockner et al. | 356/385 |
| 4,512,060 | 4/1985 | Shofner | 19/200 |
| 4,631,781 | 12/1986 | Shofner | 19/200 |
| 4,634,280 | 1/1987 | Paulson, Jr. | 356/385 |
| 4,686,744 | 8/1987 | Shofner | 19/200 |
| 4,764,876 | 1/1990 | Whitener, Jr. et al. | 73/160 |
| 4,885,473 | 12/1989 | Shofner et al. | 250/574 |
| 4,891,974 | 1/1990 | Wassenhoven | 73/160 |
| 4,982,477 | 1/1991 | Hosel | 19/0.25 |

FOREIGN PATENT DOCUMENTS

| | | | |
|---|---|---|---|
| 0226070 | 3/1958 | Australia | 73/160 |
| 225009 | 10/1987 | European Pat. Off. | 15/2 |
| 2408117 | 6/1979 | France. | |
| 02111624 | 12/1983 | Japan | 73/160 |
| 2031960 | 4/1980 | United Kingdom | 73/160 |
| 2064106 | 10/1990 | United Kingdom | 11/10 |
| WO896169 | 7/1988 | WIPO. | |

OTHER PUBLICATIONS

Steinkamp, "Flow Cytometry" Rev. Sci. Instrum. vol. 55, No. 9, Sep. 1984, pp. 1381–1384.
Shofner, Frederick M., et al., "Advance Fiber Information System: A New Technology for Evaluating Cotton," (Dec. 1988).
Lord, E. And Heap, S. A., "The Origin and Assessment of Cotton Fibre Maturity," International Institute for Cotton (Dec. 1988) pp. 1–38.
Thibodeaux, Devron, P., et al., "An Absolute Reference Method for Determination of the Maturity of Cotton Fibers," (1988).
Bragg, C. K. (1990) "A Rapid Measurement of Short Fiber Content" 20th International Conference, Bremen.

(List continued on next page.)

Primary Examiner—Vincent P. McGraw
Assistant Examiner—K. P. Hantis
Attorney, Agent, or Firm—Luedeka, Neely & Graham

[57] ABSTRACT

A testing apparatus includes a receiver for holding a plurality of textile samples and an automatic feed mechanism disposed adjacent to the receiver for selectively engaging and removing samples from the receiver and transporting them to a processor where the textile material is processed to produce textile entities in an individualized condition. The entities are then transported to a sensor that produces signals corresponding to characteristics of the entities. A control means detects the presence or absence of a sample in the automatic feed mechanism and controls it accordingly. Analog and digital components analyze the characteristic signals to identify segments of the characteristic signals that correspond to neps, trash and fibers.

14 Claims, 12 Drawing Sheets

OTHER PUBLICATIONS

Faserforshung und Textiltechnik 25 (1974) Heft–12 Zeitschrift fur Polymerforschung (pp. 528–536).

Frey, M. (1990) "Practical Experience with New Cotton Measuring Methods" 20th International Cotton Conference, Bremen, Germany. Faserinstitut Bremen e.V.

Thibodeaux, D. P. (1990) "Update of Special Applications of Cotton Maturity Testing" 20th International Cotton Conference, Bremen, Germany. Faserinstitut Bremen e.V.

Deussen, H. et al. (1988) "Why does the Need for Finer, Stronger, and Cleaner Cotton Fibers Require a Change in the Cotton Grading and Marketing System/" W. Shalfhorst & Co. Doc No. 21 Monchengladback, Germany.

Shofner, Frederick M., et al., "An Overview of the Advanced Fiber Information System," (Mar. 1990).

(Catalogue pages) "Performance, Accuracy, Efficiency: Spinlab HVI 900 System" no date.

"Fiber Testing USTER® AFIS–T Measuring Trash and Dust Particles in Cleaning and Carding" 4 pages (Sep. 1991).

"Trash Testing—MDTA 3 and AFIS–T" (prepared for ITMA 1991, Hanover).

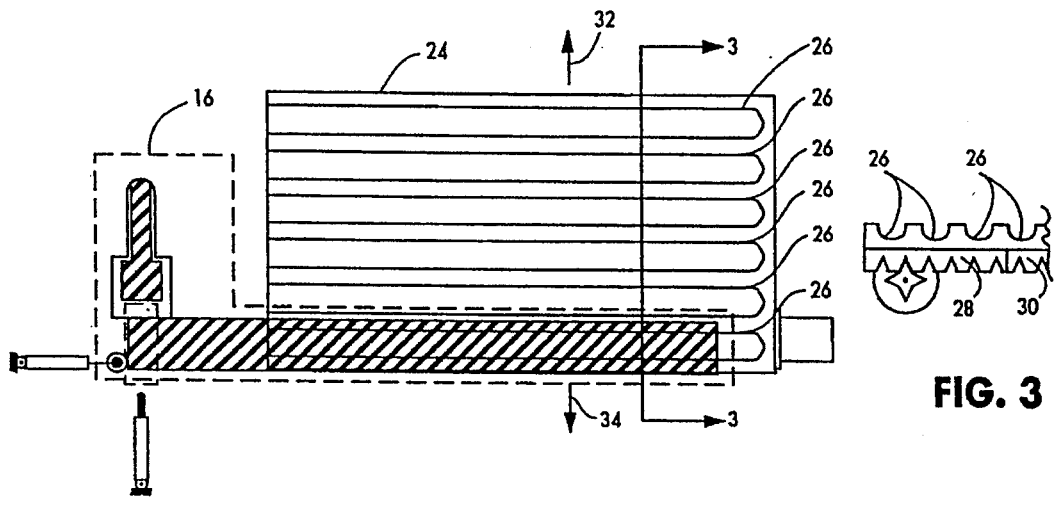
FIG. 2
FIG. 3
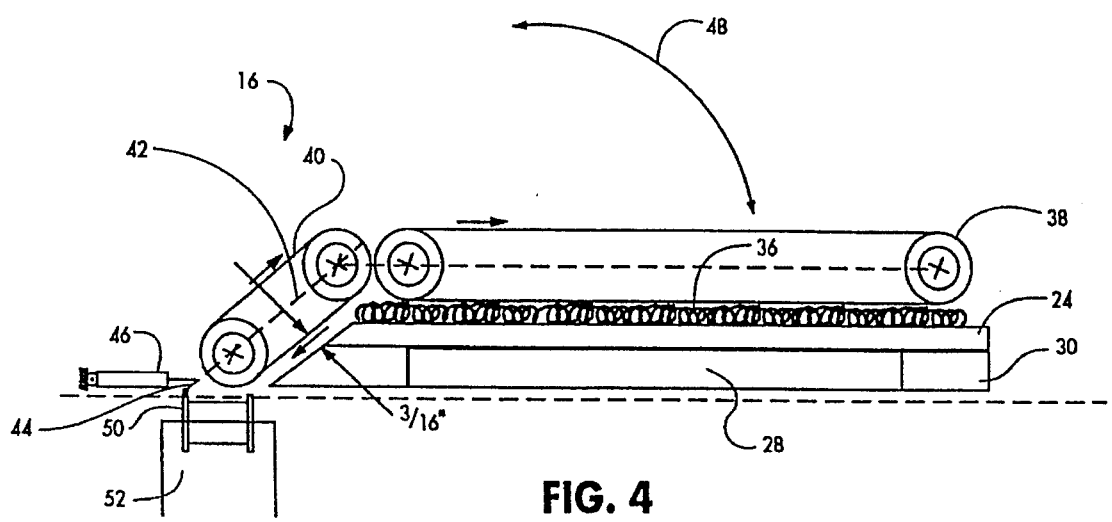
FIG. 4

Common Characteristics are Inside Circles
Distinguishing Characteristics are Outside

APPARATUS AND METHOD FOR TESTING MULTIPLE CHARACTERISTICS OF SINGLE TEXTILE SAMPLE WITH AUTOMATIC FEED

CROSS REFERENCE TO RELATED APPLICATIONS

This application is a continuation-in-part of application Ser. No. 07/493,961 filed Mar. 14, 1990, now Pat. No. 5,270,787 entitled Electro-Optical Methods and Apparatus For High Speed, Multivariate Measurement of Individual Entities In fiber or Other Samples, whose disclosure is incorporated herein by reference.

FIELD OF INVENTION

The present invention relates to instruments for testing entities, particularly individual textile entities in an airstream, and more particularly relates to a textile entity tester having an automatic feed mechanism for loading textile fiber plus entity samples and having an analyzer for distinguishing between types of entities, such as neps, trash and fibers.

BACKGROUND OF INVENTION

The predecessor instrument to the present invention is manufactured by Zellweger Uster, Inc. and is known as AFIS. This instrument separated fibers and neps into one airstream and trash into another airstream using the device disclosed in U.S. Pat. No. 4,512,060. Trash is defined as foreign matter having size greater than about 50 µm. Sometimes this foreign matter is called dust and trash but we shall use the designation trash here for simplicity. In this predecessor, AFIS, it was necessary to test three sets of replicate samples of textile material separately to determine information about fibers, neps and trash. One test and one separate sample of textile material was necessary for each type of entity for each replicate. Although this AFIS provided the best data available at the time for automated and fast textile testing instruments, there was a need for better data and increased speed. An improved sensor was discovered and is disclosed in the copending application Ser. No. 07/493,961, and the instrument incorporating the improved sensor, also known as AFIS, is manufactured by Zellweger Uster, Inc. For clarity and consistency with the references, the first instrument is called AFIS 0 and the instrument with the improved sensor is called AFIS 1.

The present invention is a further improvement in AFIS 1 and is directed primarily to testing rate considerations. It was first discovered that the improved sensor of AFIS-1 produced data that would enable substantially simultaneous measurement of multiple data from the same sample of textile material. By substantially simultaneous it is meant that nep data, fiber data and trash data are obtained by testing a single sample of textile material and detecting and measuring substantially all of the neps and trash and detecting and measuring a representative sample of the fibers. Thus, this improvement eliminates the need to run three separate tests on typically 3–5 replicates of three separate samples to obtain data for neps, trash and fiber. Also, it was discovered that such data could be obtained using only one sensor, if desired. The testing speed improvements discussed above are made possible by a new analyzer circuit, which is a hybrid analog and digital circuit in the preferred embodiment. Speed of operation is increased by a factor of three in the present invention as compared to AFIS 1 or AFIS 0.

With the increased speed or rate of testing achieved by the above described improvement, there arose a need for automation to insure timely supply of sample to the testing instrument. Specifically, there arose a need for an automatic feed mechanism that handles delicate samples, rapidly supplies them to the testing instrument and frees the operator for substantial periods of time. Such automation has not been successfully attempted previously because of the need for a long, slender, elongate sample of textile material and the perceived need to hand form the sample and gently hand feed the fragile sample into the testing instrument. The present instrument provides a new automatic feed mechanism that can handle the delicate elongate slender samples that are needed by an instrument testing textile samples.

SUMMARY OF INVENTION

The present invention solves the foregoing and other problems associated with prior art devices by providing a testing apparatus which includes a receiver and an automatic feed mechanism. The receiver is adapted and configured to hold a plurality of elongate samples of textile material. An automatic feed mechanism is disposed adjacent to an output of the receiver and selectively engages the samples in the receiver to remove the sample and transport it along a transportation path to its output. A processor receives the sample and processes the material to release the entities, including fiber, trash and neps, one from the others. This processor also individualizes the entities and produces the entities to an output in an individualized condition. A transport mechanism, preferably a conduit and an airstream within the conduit, transports the entities from the processor to a sensor where characteristic signals are produced that represent sensed characteristics of the entities.

A controller is provided for detecting the presence or absence of sample in the automatic feed mechanism and actuates the automatic feed mechanism to engage and transport a sample to the processor when the absence of a sample is detected and when the processor has completed processing of the previous sample. Of course, a delay interval may be introduced to help eliminate any overlap between the processing of a previous sample and the introduction of the next sample.

The receiver includes a magazine with a plurality of elongate receptacles formed in the magazine for holding the elongate samples. An indexing support is provided for supporting and moving the magazine to selectively position one of the elongate receptacles adjacent to the receiver output and adjacent to the automatic feed mechanism. The controller is operable to selectively actuate the indexing mount to move and index a selected one of the elongate receptacles into registry with the automatic feed mechanism. In the preferred embodiment, an analyzing means is provided for receiving the characteristic signals representing characteristics of entities that were sensed. The analyzer analyzes the characteristic signals to identify segments of the signals that correspond to a particular type of entity. For example, the analyzer will identify a particular segment of the characteristic signal as being producing by either a nep, trash, or a fiber.

In the preferred embodiment, the analyzer first looks at the amplitude of the characteristic signals and, if the signal is above a certain amplitude, it corresponds to either neps, trash or fiber. To distinguish between trash and neps, the analyzer compares an extinction signal corresponding to extinction caused by a sensed entity, to a forward scatter signal, corresponding to light scattered forward by a sensed entity. If the ratio of the forward scattered signal to the extinction signal is greater than about one-half, the analyzer determines the entity to be a nep. If it is less than one-half, the entity is determined to be trash.

To distinguish between fiber and small trash, the analyzer looks at the entity speed. The analyzer will determine the speed of the entity from the characteristic signals and will identify the signal segment as either trash or fiber based on that speed. In the preferred embodiment where the gas flow is Mach 0.3 or about 100 m/s, any entity having a speed of 50 meters per second or greater is considered to be fiber. Other classification criteria are of course used by software.

BRIEF DESCRIPTION OF THE DRAWINGS

The present invention may best be understood by reference to the following Detailed Description of preferred embodiments when considered in conjunction with the Drawings in which:

FIG. 2 is a somewhat diagrammatical cross-sectional view of an automatic feed mechanism including a magazine;

FIG. 3 is a somewhat diagrammatical cross-sectional end view of the magazine shown in FIG. 2;

FIG. 4 is a somewhat diagrammatic cross-sectional view of the feed head and magazine;

DETAILED DESCRIPTION

Figure 1:
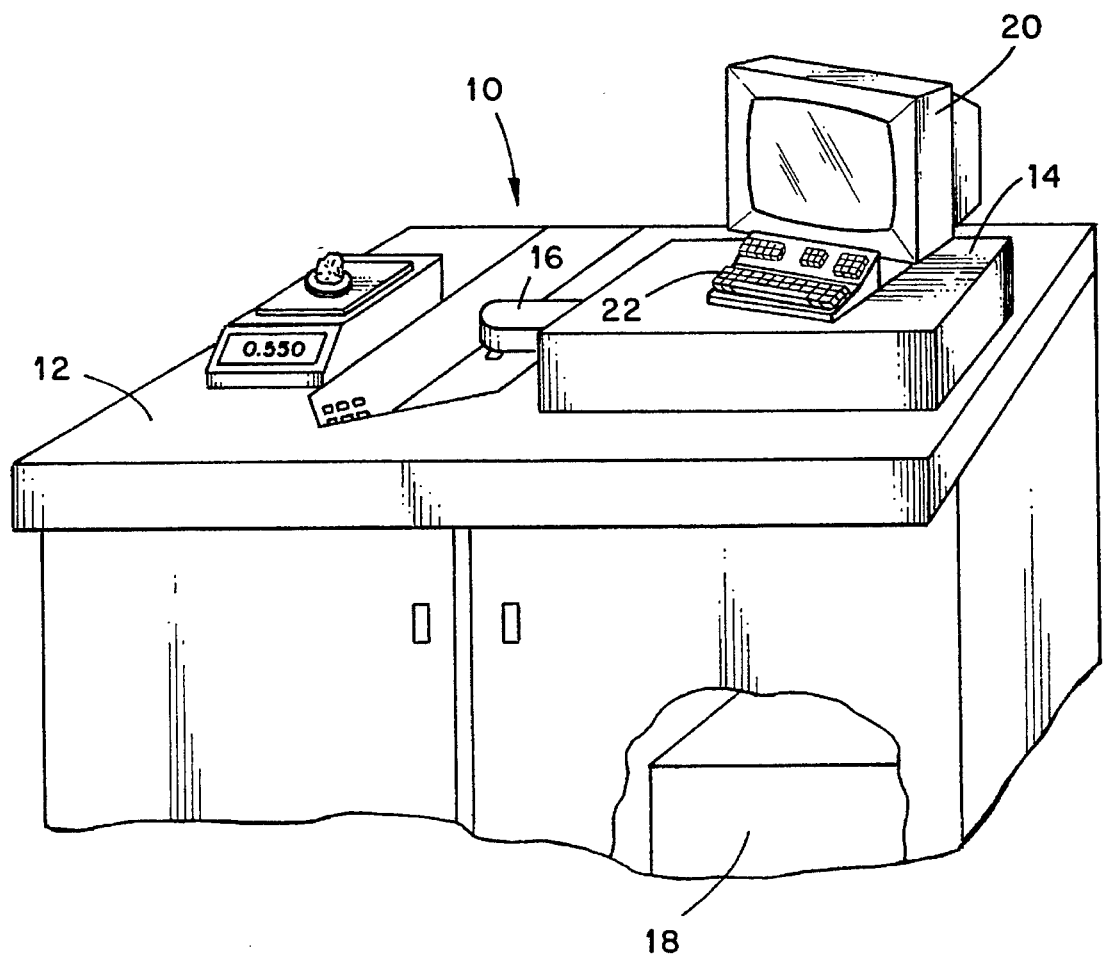
FIG. 1 is a perspective view of the exterior of a fiber testing apparatus, a preferred embodiment of the present invention.

Referring now to the drawings in which like reference characters designate like or corresponding parts throughout the several views, there is shown in FIG. 1 an external view of the textile testing apparatus 10 constituting a preferred embodiment of the present invention. The testing apparatus 10 includes a main housing 12 with an automatic carousel 14 mounted on the top of housing 12 for holding textile material samples. A feed head 16 extends from the carousel 14 for loading textile samples into the testing apparatus 10.

The operation of the testing apparatus 10 is under control of a computer 18 which interfaces with the operator through a display 20 and a keyboard 22. In the preferred embodiment, the testing apparatus 10 is used to test textile materials and is particularly designed to measure the characteristics of textile fibers, neps and trash, but the testing apparatus 10 would be equally operable on any entity having size and weight characteristics that are comparable to the aforementioned textile entities.

Referring now to FIG. 2, a somewhat diagrammatic top view of a magazine 24 and feed head 16 is shown. The magazine 24 is contained within the carousel 14 shown in FIG. 1, and it includes a plurality (20 to 200) of receptacles 26 that extend the length of the magazine 24 and accept elongate samples of textile materials. In FIG. 3, a cross-sectional diagrammatic view of a portion of the magazine 24 is shown. As best shown in FIG. 3, the receptacles 26 are channels formed in the magazine 24 to a depth of approximately one inch and having a horizontal width of approximately one inch. The magazine 24 is carried on a rack 28 that is driven by a stepper motor 30 to move the rack horizontally in the directions indicated by arrows 32 and 34 in FIG. 2. Thus, the stepper motor 30 selectively moves magazine 24 (or indexes the magazine 24) horizontally to align a desired receptacle 26 with the feed head 16. Once the desired channel 26 is in proper registry with the feed head 16, the sample within that particular receptacle 26 is removed by the feed head 16 and delivered to the testing apparatus 10 for testing.

Referring now to FIG. 4, a diagrammatic side cross-sectional view of the feed head 16 and the magazine 24 is shown. As shown in FIG. 4, an elongate slender textile sample 36 is positioned on the magazine 24 in one of the receptacles 26. The sample 36 is engaged by feed head belts 38 and 40 which are mounted on a frame represented by dashed line 42. The frame 42 is pivotally mounted on a pivot pin 44 and the position of the frame 42 is controlled by a piston and cylinder set 46 which raises and lowers the frame 42 along the arc indicated by arrow 48. Thus, the piston and cylinder set 46 is operable to lower the belts 38 and 40 into engagement with the sample 36 and raise the belts 38 and 40 away from the sample 36 and magazine 24 so that the magazine 24 may be moved without interference from the belts 38 and 40. The belts 38 and 40, when they engage the sample 36, drive the sample 36 into a top feed roll 50 which, in turn, delivers the sample to a feed tray 52.

Figure 5:
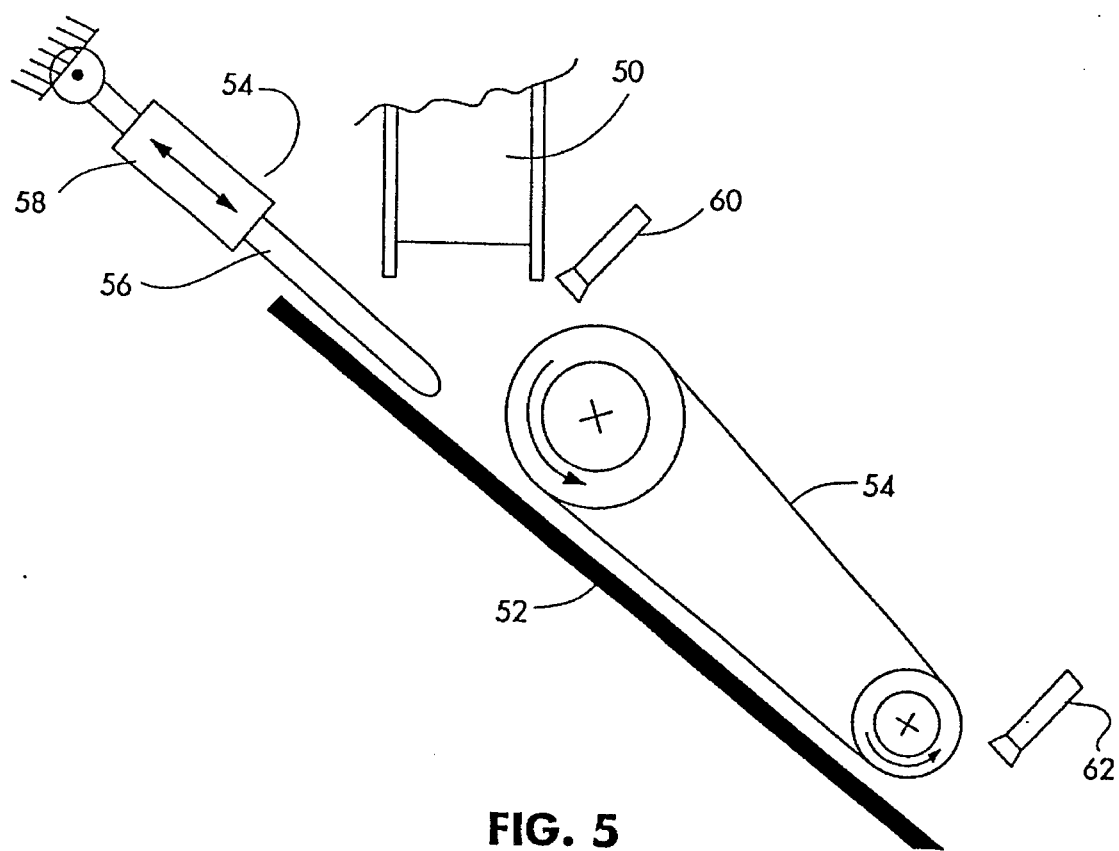
FIG. 5 is a somewhat diagrammatical side cross-sectional view of a feed finger and feed rollers.

Referring now to FIG. 5, a side view of the tray 52 is shown. The top feed roller 50 delivers the sample to the feed tray 52 and a plunger 53 engages and drives the sample under a tray feed belt 54 which is mounted immediately above and parallel to the feed tray 52. The tray feed belt 54 drives the sample down the feed tray 52 and is the last step performed in the automatic feed head 16 of the testing apparatus 10. Optical sensors 60 and 62 are provided for detecting the presence or absence of a sample 36 of textile material in the feed mechanism 16. Sensor 60 is positioned at the output end of the feed belt 50 viewing the feed tray 52 in the area of the feed tray that is traversed by the plunger finger 56. Optical sensor 62 is positioned at the end of the tray feed belt 54 viewing the feed tray 52.

In FIGS. 2, 3, 4, and 5 it will be understood that the illustrations of feed belts 38, 40, 50, and 54 represent the drive mechanisms, including motors, controls, and interconnections therefor, that are necessary to operate a feed belt in a conventional manner. Likewise, the representations of optical sensors 60 and 62 represent conventional sensors with conventional power supplies and control interconnections. Again, the piston and cylinder set 46 and the plunger 54 comprised of a dual action piston and cylinder set 58 and plunger finger 56 represent conventional piston and cylinder sets, including compressed air supplies and control mechanisms.

Figure 6:
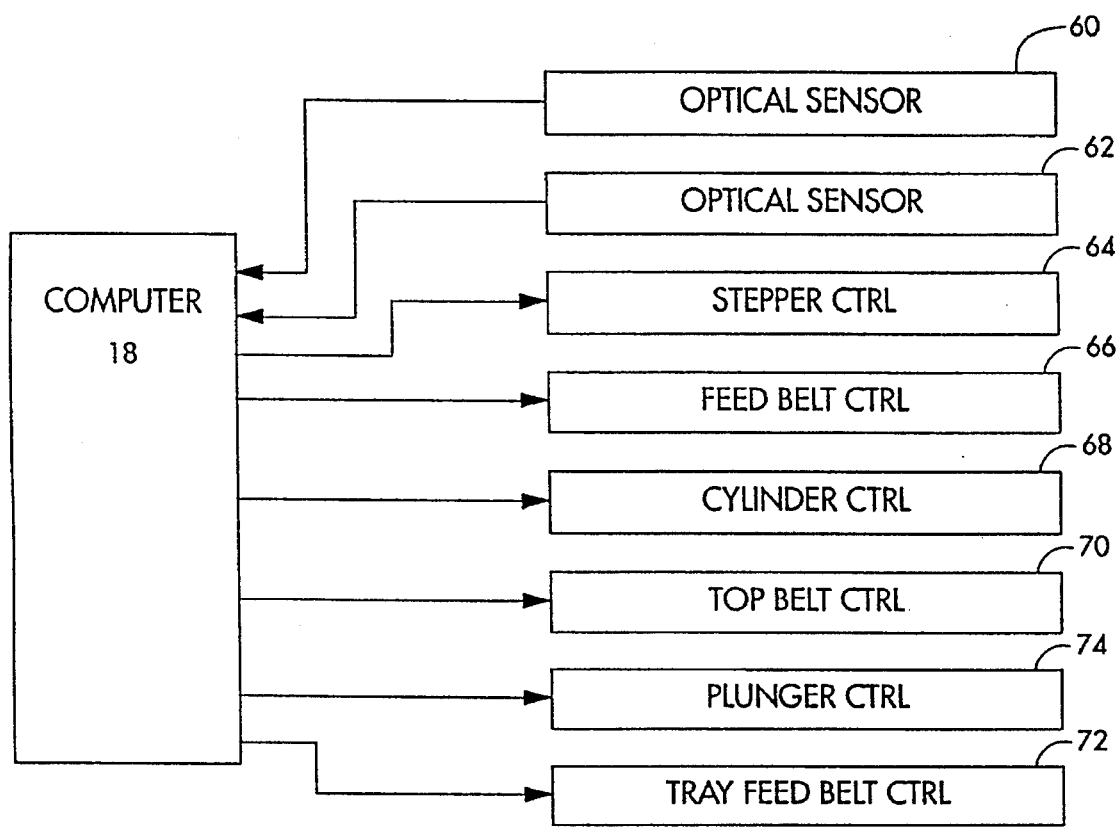
FIG. 6 is a block diagram of the computer and control system for operating the automatic feed mechanism.

The operation of these elements including their control elements may best be understood by reference to FIG. 6, a block diagram illustrating the computer 18 and control mechanisms used in the automatic feed head 16. Referring to FIGS. 2–6, when the testing apparatus 10 is turned on, the computer 18 issues a command to the stepper control 64 to drive the magazine 24 to its initial position aligning the first receptacle 26 with the automatic feed mechanism 16. When the magazine 24 is in the desired position, the computer 18 issues commands to the feed head belt control 66 and the cylinder control 68 which turns on the feed belts 38 and 40 and actuates the cylinder 46 to lower the belt 38 into engagement with the sample 36. The computer 18 also issues a start command to the top belt control 70 and the tray feed belt control 72 and thereby starts the operation of the top feed belt 50 and the tray feed belt 54.

After the computer 18 initiates commands that will cause the feed belts 38, 40 and 50 to deliver a sample to the feed tray 52, the computer 18 will monitor the signal from sensor 60 and, when a sample is detected on the tray 52, the computer 18 will issue commands to the plunger control 74 actuating the cylinder 58 of the plunger 54 to move the plunger finger 56 forward toward the tray feed roller 54 and drive the sample 36 on the tray 52 under the feed belt 54. If the computer 18 does not detect the presence of a sample at the sensor 62 within about one and one-half seconds after the plunger finger 16 has been actuated, the computer will issue another command to the plunger control 74 to actuate and cause the plunger finger 56 to force the sample under the tray feed roll 54. This process will be repeated five times and, if the sensor 62 does not sense the sample after the fifth repetition, the computer 18 will issue commands to stop all action of the feed mechanism 16 and display a fault condition on display 20 suggesting a sample jam in the feed mechanism.

Assuming there has been no jam, the computer 18 then analyzes the signals from the optical sensors 60 and 62 to determine whether a sample is present in the automatic feed mechanism 16. Under normal conditions, both sensors will indicate a presence of a sample 36. If neither sensor detects a sample, the computer 18 will wait another 10 seconds and analyze the signals from the optical sensors 60 and 62 again. If no sample 36 is detected by either sensor, the computer 18 will issue a command to the control cylinder 68 to raise the frame 42 and the feed belts 38 and 40 away from the magazine 24. Then, the computer 18 will issue a command to the stepper control 64 causing the stepper motor 30 to index the magazine 24 to align the second receptacle 26 with the feed mechanism 16. The computer 18 will then, again, issue commands to the cylinder control 68 to lower the feed belts 38 and 40 into engagement with a sample in the second receptacle 26. Again, the computer 18 will analyze the signals from the optical sensor 60 and 62 to determine the presence or absence of a sample and will continue indexing the magazine 24 forward until a sample is detected in the feed mechanism 16.

Assuming both optical sensors 60 and 62 initially sense the presence of a sample 36 in the feed mechanism 16, eventually the sample will be fed completely through the feed mechanism. The computer 18 periodically polls the signals from the optical sensors 60 and 62 and, when these sensors 60 and 62 indicate the absence of a sample 36 in the feed mechanism 16, it will wait for a predetermined dwell period, approximately ten seconds, and will check other operations of the testing apparatus 10. Assuming everything is functioning normally, after the dwell period the computer 18 will issue commands to the cylinder control 68 and the stepper control 64 to cause the magazine 24 to be indexed forward to the next receptacle 26.

When the sample from the last receptacle 26 has been loaded by the feed mechanism 16, or an attempt to do so has been made, the computer 18 assumes that the magazine 24 is now empty and it will display a prompt on the display 20 requesting the operator to reload the magazine 24 with textile samples and re-initiate the automatic feed process.

Figure 7:
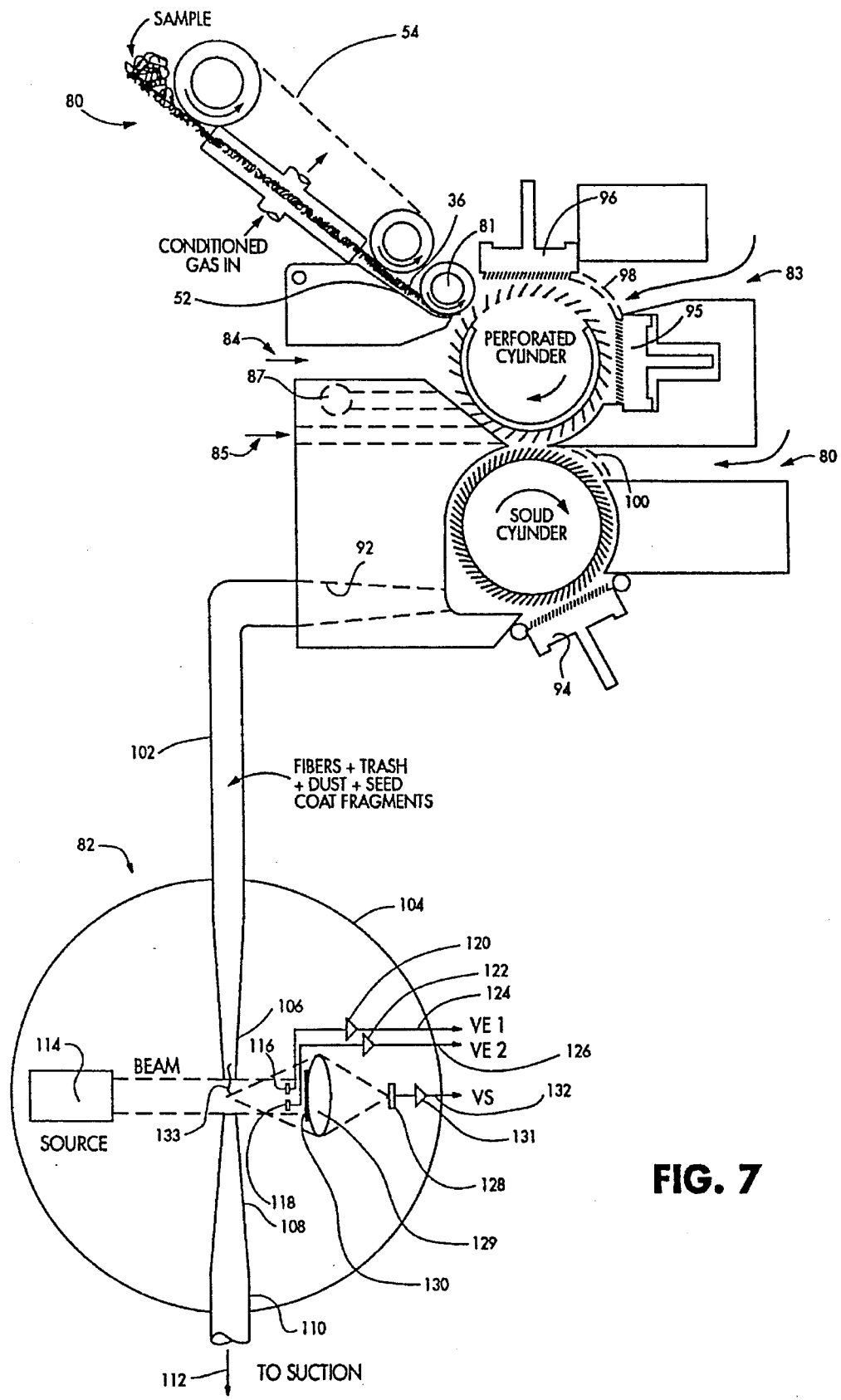
FIG. 7 shows an embodiment of an entity individualizer that receives samples from the automatic feed mechanism and a single sensor that receives entities from the individualizer.

Referring now to FIG. 7, there is shown a fiber individualizer 80 and a sensor 82. The individualizer 80 receives textile samples 36 from the feed tray 52 and feed tray belt 54. The function of the individualizer 80 is to release and individualize entities that are fed to it. In the preferred embodiment, the individualizer 80 releases neps, trash and fibers one from the others and individualizes the various types of entities.

The individualizer 80 includes a feed roller 81 that receives the sample on the feed tray 52 and feeds the sample 36 into the individualizer 80. Conditioned air is input into the individualizer through air supply channels 83, 84, 85 and 86. (Compressed air which purges or cleans the individualizer is supplied for brief periods, such as 0.5 seconds, via channel 87.) The sample 36 is fed in a controlled manner to the individualizer 80 by the feed roller 81 and the entities are processed by the perforated cylinder 88 and the solid cylinder 90 in combination with the carding flats 94, 95 and 96. This processing releases the entities, such as neps, fibers, and trash, one from the others, and individualizes the entities so that the entities are delivered one at a time (in an individualized condition) at the output 92 of the individualizer 80.

The individualizer 80 is substantially the same as that disclosed in U.S. Pat. No. 4,512,060 and that disclosure is incorporated by reference. The major difference in construction of the individualizer 80, as compared to U.S. Pat. No. 4,512,060, is the provision of staggered double baffles 98 and 100 that are provided across air supply channels 83 and 86. The baffles 98 and 100 allow air to flow into the individualizer through the baffles plates 98 and 100, but the plates 98 and 100 prevent trash or other particles from being thrown out of the individualizer through the air passages 83 and 86. Thus, in contrast to the individualizer shown in U.S. Pat. No. 4,512,060, all of the entities that are processed by the individualizer 80 are output through the individualizer output 92 and into a conduit 102. The conduit 102 carries the entities in an airstream into a sealed chamber 104. The end of the conduit 102 terminates in a nozzle 106 and an opposing nozzle 108 is positioned in the chamber 104 in substantial alignment with the nozzle 106 such that an opening is formed between the two nozzles 106 and 108. The nozzle 108 is connected to conduit 110 which, in turn is connected to a vacuum source 112 that provides the vacuum and creates the airstream in the conduits 102 and 110 and the nozzles 106 and 108. A source of light 114 is provided in the chamber 104 and directs light through the opening between the nozzles 106 and 108 toward two extinction detectors 116 and 118 that are positioned side by side as shown in FIG. 7. With respect to the airstream in the nozzles 106 and 108, detector 118 is positioned downstream from the detector 116. The outputs of the detectors 116 and 118, are fed through amplifiers 120 and 122, respectively, and output extinction signals VE1 and VE2 are produced on lines 124 and 126.

A forward scatter detector 128 including a lens system 129 and a light stop 130 is provided for detecting light that is scattered forward at an angle of about 40° (in the preferred embodiment) by entities 133 passing through the opening between nozzles 106 and 108. The output of the forward scatter detector 128 is applied through an amplifier 131 to produce a forward scatter signal, VS on line 132.

The sensor 82 as described above is substantially identical to the sensor described in application Ser. No. 07/493,961 now U.S. Pat. No. 5,270,787 whose description is incorporated herein by reference.

Figure 8:
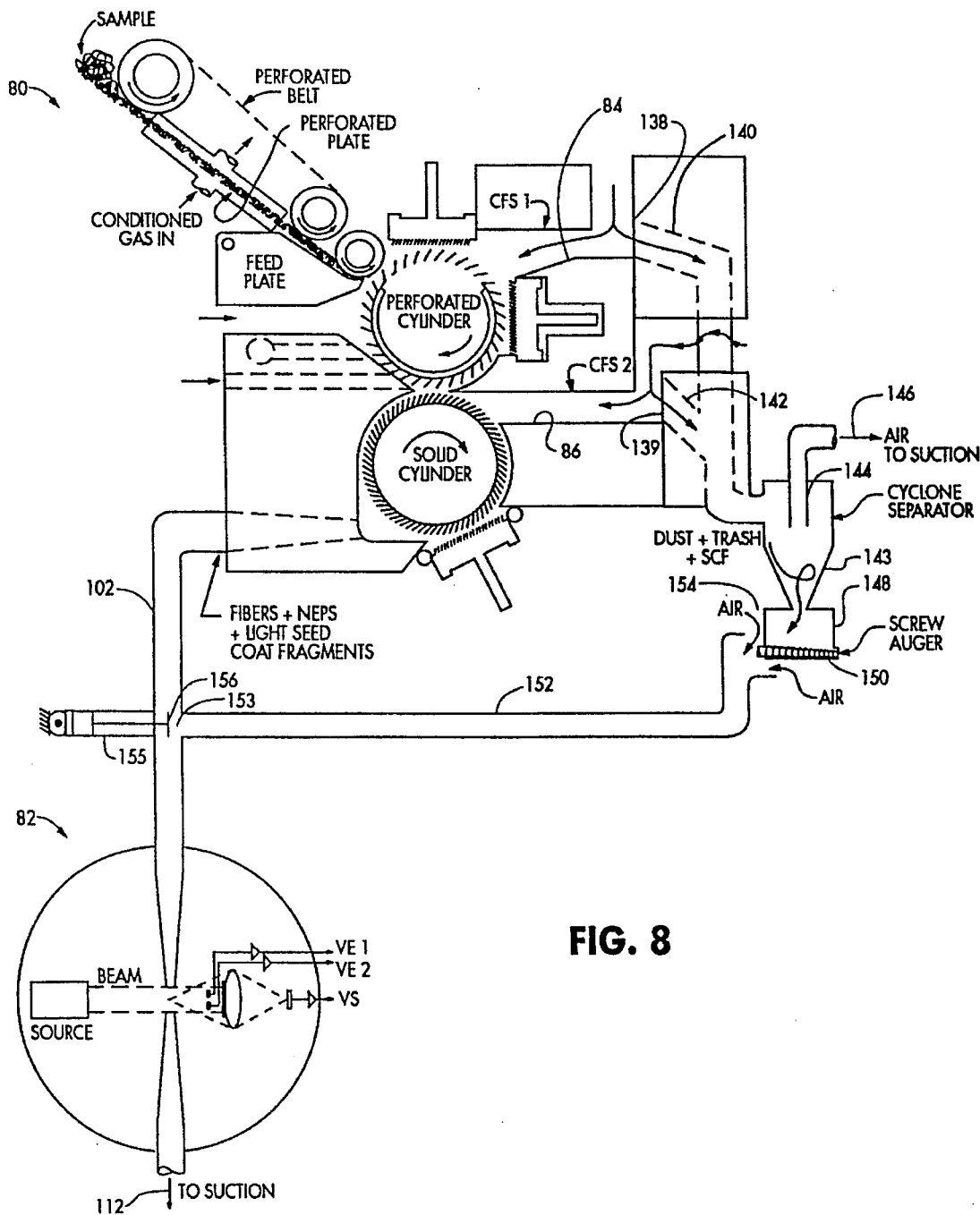
FIG. 8 is a somewhat diagrammatical view of an alternate embodiment of the individualizer and sensor system.

FIG. 8 represents an alternate embodiment combining the individualizer 80 and sensor 82. In this embodiment, the sensor 82 is identical to that shown and described in FIG. 7 and the individualizer 80 is substantially identical to that described in U.S. Pat. No. 4,512,060, except in the manner in which trash is handled after it leaves the individualizer 80. In the embodiment of FIG. 8, the baffles 98 and 100 are not used and trash is ejected through the air channels 84 and 86, counterflow slots, CFS. The cylinders 88 and 90 propel the trash particles through the passageways 84 and 86 in opposition to the airflow therein. When the trash particles reach the air intakes 138 and 139 their momentum carries them into the conduits 140 and 142 and they are transported in an airstream flowing away from the individualizer 80. The conduits 140 and 142 are input to a cyclone separator 143 that includes a vertical conduit 144 extending upwardly to an air suction 146. The suction 146 provides the suction needed to form the airstream in conduits 140 and 142. Air and very fine particles leave the separator 143 through the conduit 144 but most of the dust and trash particles are separated by outward centrifugal forces and settle by gravity into the chamber 148 and are selectively ejected from the chamber by an auger 150.

Upon command from the computer 18, the trash particles are augured out of the chamber 148 where they are picked up by an airstream in a conduit 152. An air intake 154 is provided adjacent to the auger output. The airstream in the conduit 152 carries the trash particles to an intake 153 in the conduit 102. A piston and cylinder set 155 selectively covers and uncovers the intake 153 with a cover plate 156 mounted on the piston and cylinder set 154. The piston and cylinder set and the auger 150 are under the control of the computer 18. When it is desired to measure the characteristics of fibers and neps, the cover plate 156 is moved against the intake 153 and fibers and neps are supplied to the sensor 112 substantially without trash content. Then, when it is desired to measure trash characteristics, the computer 18 actuates the piston and cylinder set 154 to uncover the intake 153 and the computer 18 actuates the auger 150 to begin ejecting dust and trash from the chamber 148. The suction 112 then also creates an airstream in the conduit 152 that carries the trash particles through the conduit 152, into the conduit 102 and finally through the sensor 82.

Figure 9:
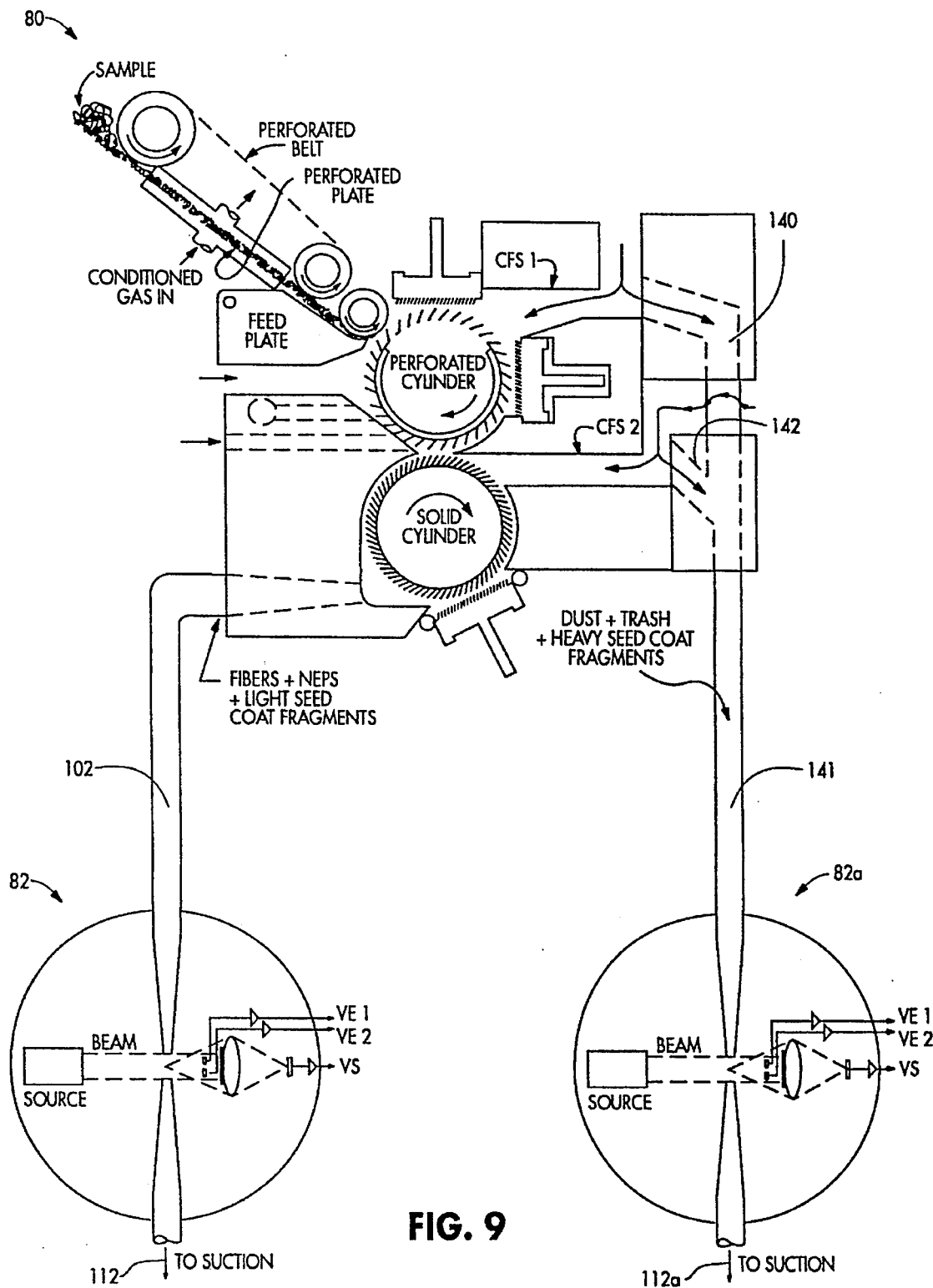
FIG. 9 is another embodiment of the individualizer and sensor system.

Yet another alternate embodiment is shown in FIG. 9. In this embodiment, the individualizer 80 is substantially the same as that shown in U.S. Pat. No. 4,512,060 except that the conduits 140 and 142 are combined into a single conduit 141 and connected to a separate sensor 82a. The airstream in conduit 141 is provided by a suction 112a that is approximately identical to the suction 112 of sensor 82.

The application of the above three embodiments represented by FIGS. 7, 8 and 9 can be best understood in light of the operation of the sensor, the data acquisition boards, and the computer 18 which are described below.

Figure 10:
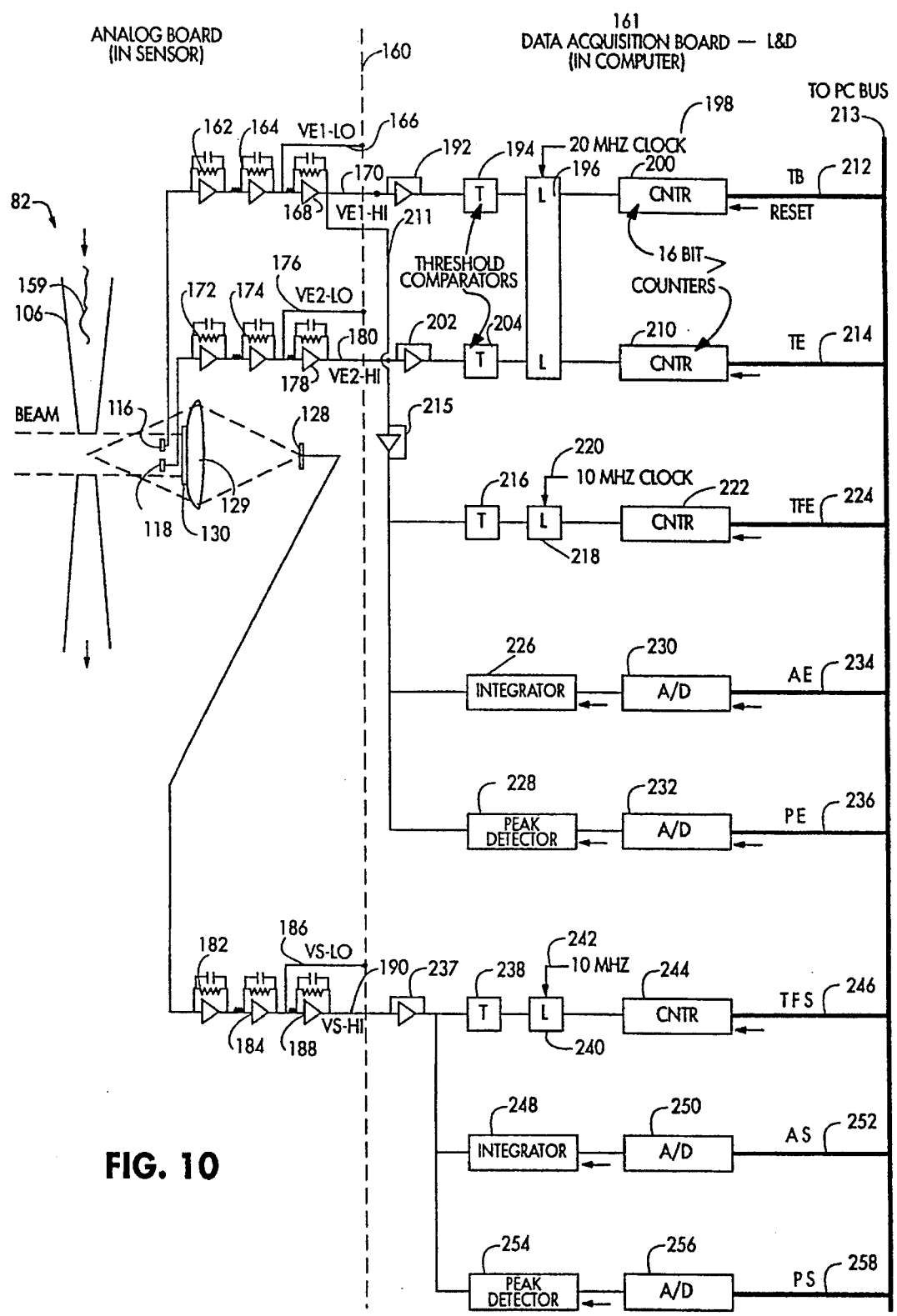
FIG. 10 is a block diagram of the analyzer system showing the detectors and analog amplifiers of the sensor and one data acquisition board.

In FIG. 10, a schematic diagram of the sensor 82 and one data acquisition board (DAB) 161, a dashed line 160 indicates the physical division between the sensor 82 and a data acquisition board (DAB) 161, shown here as a DAB responding to an individual fiber 159 moving in nozzle 106. Referring to the left hand side of FIG. 10, the sensor 82 is shown in greater detail. An extinction sensor 116 provides an output to an trans-impedance amplifier 162 whose output is amplified by an amplifier 164 having a voltage gain Of approximately 4.3. The output of amplifier 164 appears on line 166 and constitutes the low gain channel of the first extinction sensor (VE1-LO). The output of amplifier 164 is applied through amplifier 168 having a gain of 12.5 and the output of amplifier 168 appearing on line 170 constitutes the high gain channel of the first extinction signal (VE1-HI).

In a similar construction, the output of the second extinction sensor 118 is applied through a trans-impedance amplifier 172 to a voltage amplifier 174 having a gain of about 4.3. The output of amplifier 174 appears on line 176 and constitutes the low gain channel of the second extinction signal (VE2-LO). The output of amplifier 174 is also applied through an amplifier 178 having a gain of about 12.5 and the output of amplifier 178 appears on line 180 and constitutes the high gain channel of the second extinction signal (VE2-HI).

The forward scatter sensor 128 produces a signal that is provided to a trans-impedance amplifier 182 whose output is provided to an amplifier 184 having a voltage gain of about 20. The output of amplifier 184 appears on line 186 and constitutes the low gain channel of the scatter signal (VS-LO). The output of amplifier 184 is also applied through amplifier 188 having a gain of about 12.5 and the output of amplifier 188, appearing on line 190, constitutes the high gain channel of the scatter signal (VS-HI).

Referring now to the right hand side of FIG. 10, the data acquisition board (DAB) 161 may be described in detail. The data acquisition board (DAB) 161 shown in FIG. 10 is connected for measuring characteristics of textile fibers, as opposed to neps or trash. In this arrangement, the high gain channel of the first extinction signal appearing on line 170 is applied through an inverting isolation amplifier 192 having a gain of −1 and then to a threshold comparator 194. The threshold comparator 194 goes high or turns on when the signal appearing at its input exceeds a predetermined value, preferably one-half volt, and the comparator 194 goes low or turns off again when the signal drops below 0.5 volts.

The output of the comparator 194 is applied to a logic chip 196 that also receives a twenty megahertz clock signal 198. The logic chip 196 selectively applies the twenty megahertz clock signal to a counter 200.

In like manner the high gain channel of the second extinction signal (VE2-HI) from sensor 118 appearing on line 180 is applied through an inverting isolation amplifier 202, a threshold comparator 204, the logic chip 196 and a counter 210.

In this construction, the counts appearing in counter 200 are applied through lines 212 to a computer bus 213 via data bus directional drivers and are referred to as TB. Likewise, the counts appearing in counter 210 are applied to a computer bus 213 through lines 214 and are known as TE.

Logic chip 196 applies clock pulses to the counter 200 beginning when threshold comparator 194 goes high and ending when threshold comparator 204 goes high. Chip 196 applies clock pulses to counter 210 beginning when threshold comparator 194 goes low (after previously going high) and ending when comparator 204 goes low (after previously going high).

The high gain extinction signal is also applied through line 211 and an inverting isolation amplifier 215 to a threshold comparator 216 that controls a logic chip 218. A ten megahertz clock signal on line 220 is also supplied to the logic chip 218 and under the control of the threshold comparator 216, the logic chip 218 applies the ten megahertz clock signal to a counter 222. The count of counter 222 is applied through lines 224 to a computer bus 213 and is known as TFE.

The inverted high gain first extinction signal appearing at the output of amplifier 215 is also applied to an integrator 226 and a peak detector 228 whose outputs are applied to analog to digital (A/D) convertors 230 and 232, respectively. The output of A/D converter 230 appears on lines 234 and is applied to the bus 213 and, likewise, the output of A/D convertor 232 is applied on lines 236 to the bus 213. These data are known as area from the extinction signal AE and peak amplitude of the extinction signal PE, respectively.

The high gain channel of the forward scatter signal appearing on line 190 is applied through inverting isolation amplifier 237 to a threshold comparator 238, an integrator 248, and a peak detector 254. The output of the threshold comparator 238 is applied to a logic chip 240 that also receives a ten megahertz signal on line 242. The logic chip 240 applies clock signals to a counter 244 when the output of isolation amplifier 237 exceeds one-half volt and, when the signal falls below one-half volt, the logic chip 240 stops applying the clock signal to the counter 244. The output of the counter 244 is applied through lines 246 to the bus 213 and is known as TFS.

The outputs of the integrator 248 are applied through an A/D convertor 250 and lines 252 to the bus 213 and, likewise, the output of peak detector 254 is applied through an A/D convertor 256 and lines 258 to the bus 213. They are known as AS and PS, respectively.

From the description set forth above, it should be appreciated that TB appearing on line 212 represents the time required for the beginning of an entity, a fiber in this case, to pass from an optical projection of sensor 116 to an optical projection of sensor 118. Thus, TB corresponds to the speed of the leading edge of the entity. TE appearing on lines 214 represents the time required for the trailing end of an entity to pass from an optical projection of sensor 116 to sensor an optical projection of 118 and, thus, corresponds to the speed of the trailing end of the entity. TF appearing on lines 224 represents the time required for an entity to pass completely by an optical projection of extinction sensor 116. Thus, the TF corresponds to a dimension of the entity (such as the length of a fiber) and this dimension can be calculated based upon the speed of the entity. The signal appearing on line 234 represents the time integral of the light extinguished by the entity, or the area under the waveform, AE. The number appearing on line 236 represents the peak amount of light extinguished by the entity or to the peak amplitude PE. The count, TFS appearing on lines 246 represents the time required for the entity to pass by an optical projection of the scatter sensor 128 and corresponds to a dimension (such as length) of the entity as measured by the scatter sensor 128. The signal appearing on line 252 represents the time integral of light scattered by the entity as detected by sensor 128, AS, and the signal appearing on line 258 represents the peak amount of light scattered by the entity, PS.

The function of the DAB 161 is seen to convert the analog signals from the electro-optical (E-0) sensor 82 into digital signals impressed on the computer bus 213 and designated as TB 212, TE 214, TFE 224, etc. These signals thus define E-0 parameters. The E-0 parameters, in turn, are used to provide entity information, fiber length and diameter in the case of FIG. 10. Application Ser. No. 07/493,961 now U.S. Pat. No. 5,270,787 which focuses on the AFIS 1 sensor, generally discloses how length, diameter, fineness, or maturity information for individual fiber entities is determined. That application also discloses how sensor 82 provides nep or trash entity signals. Application Ser. No. 07/762,905 now U.S. Pat. No. 5,321,496 further discloses how a sensor 82 enables trash measurements and, in particular, how such measurements are interpreted.

It can thus be appreciated that the DAB 161 of FIG. 10 represents a major improvement in signal processing capability. Further, instruments based on earlier disclosures were unable to simultaneously provide multiple entity data—fiber, neps, trash, etc—from a single sample. The DAB 161 of FIG. 10 enables that possibility, as will now be explained, for the preferred embodiment of FIG. 7.

Figure 11:
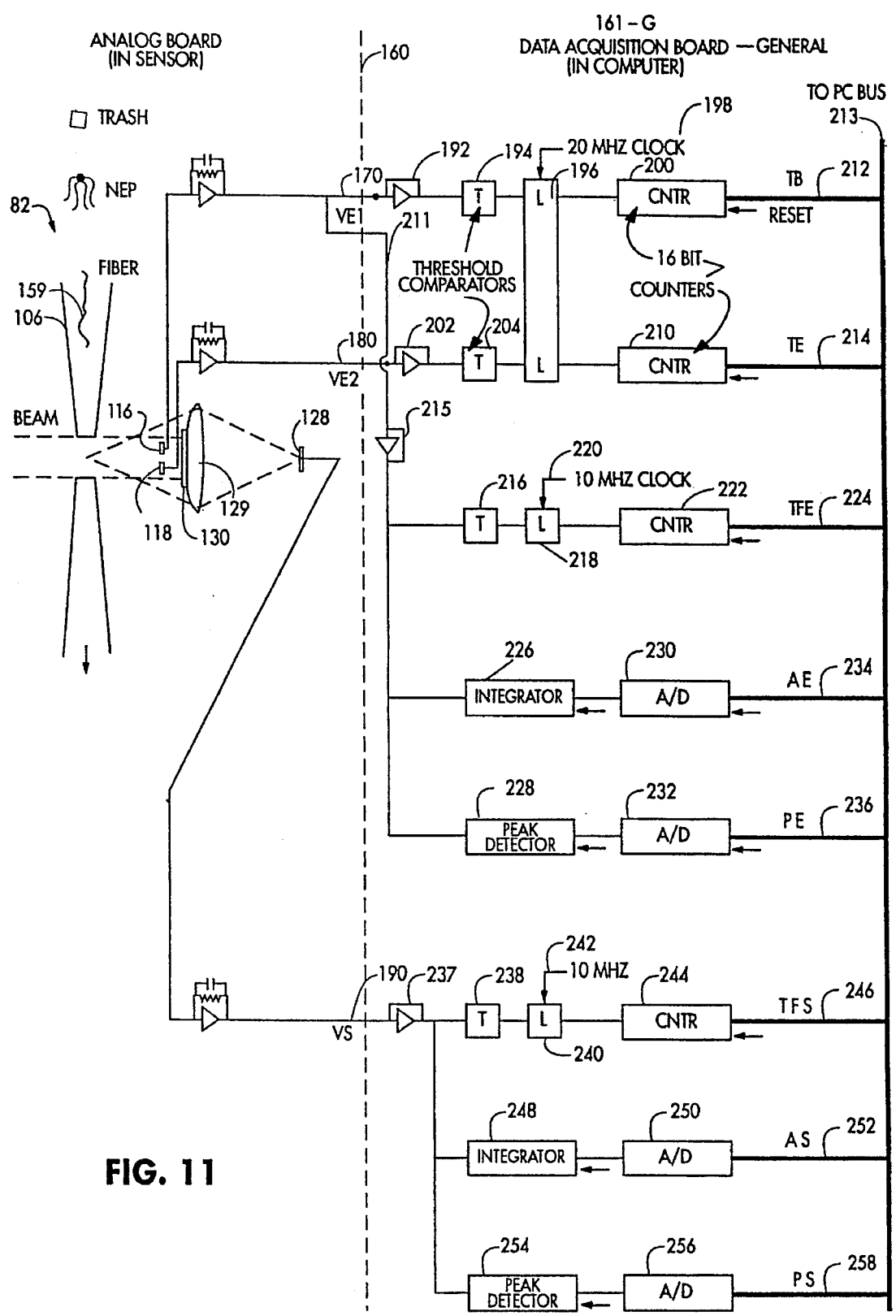
FIG. 11 is a generalized block diagram derived from FIG. 10.

In FIG. 7, sensor 82 receives and responds to all individualized entities transported by conduit 102. One must therefore examine the entity signals or waveforms themselves and determine whether the entity is a fiber, a nep, or a trash particle. It has been discovered that the improved sensor means, as disclosed in Application Ser. No. 07/493, 961, now U.S. Pat. No. 5,270,787 in combination with improved signal processing means (i.e. DAB 161 in FIG. 10) enables such classification and, thereby, meets the single sample/multiple data products objective. Whereas FIG. 10 describes in detail DAB operation for determination of length and diameter of individual fibers, FIG. 11 generalizes to show how signals from multiple entities are measured and, importantly, classified. To simplify FIG. 11, the low gain/high gain distinction is disregarded. This means that all signal voltages levels given below are referred to the high gain channel. The digital processing times (A/D conversions, resets, etc.) are also disregarded, so that all entities are examined. Accordingly, the arrival of an entity in the beam of sensor 82 will lead to analog signals shown in FIG. 12 and the corresponding digital signals TB, TE, TF, etc on line 212, 214, 222, etc. of FIG. 11.

Figure 12:
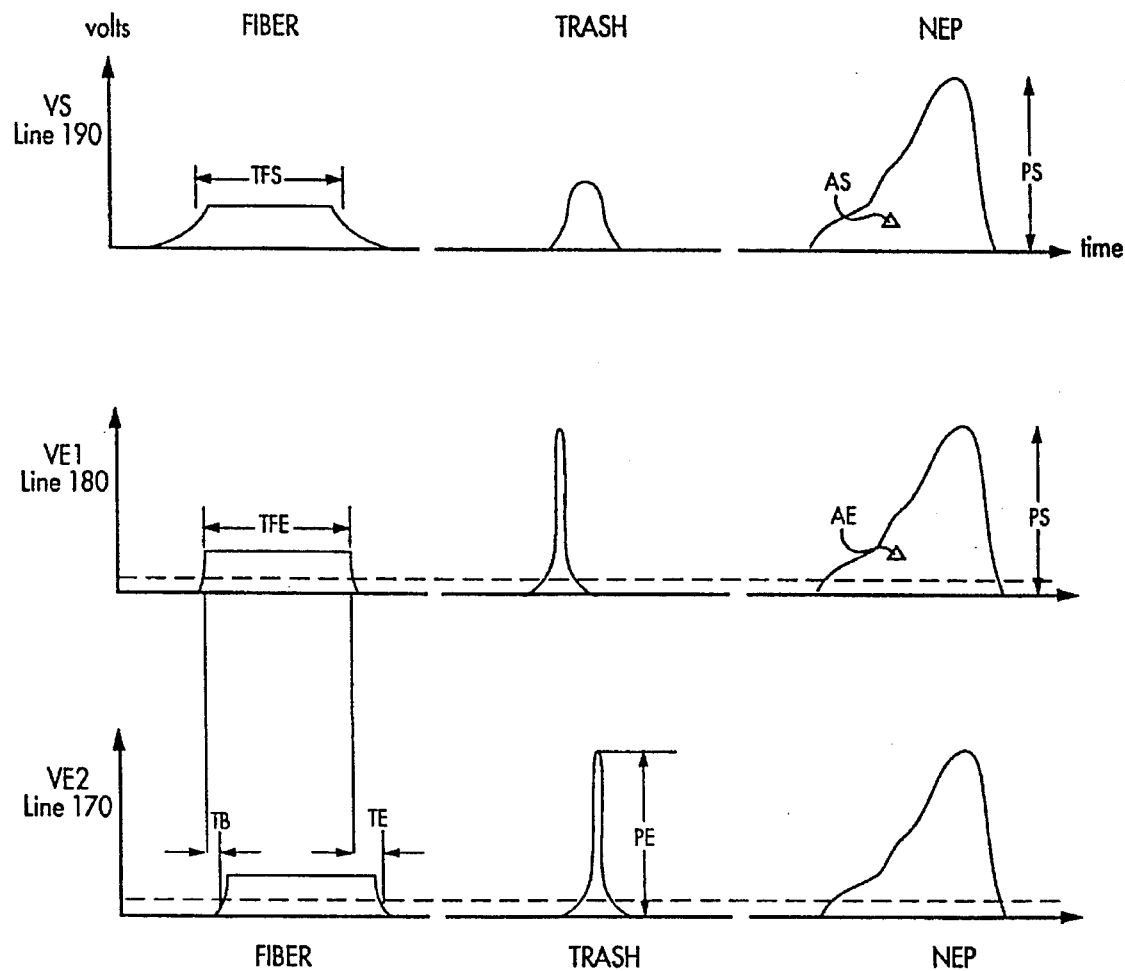
FIG. 12 shows analog waveforms from the sensor.
Figure 13:
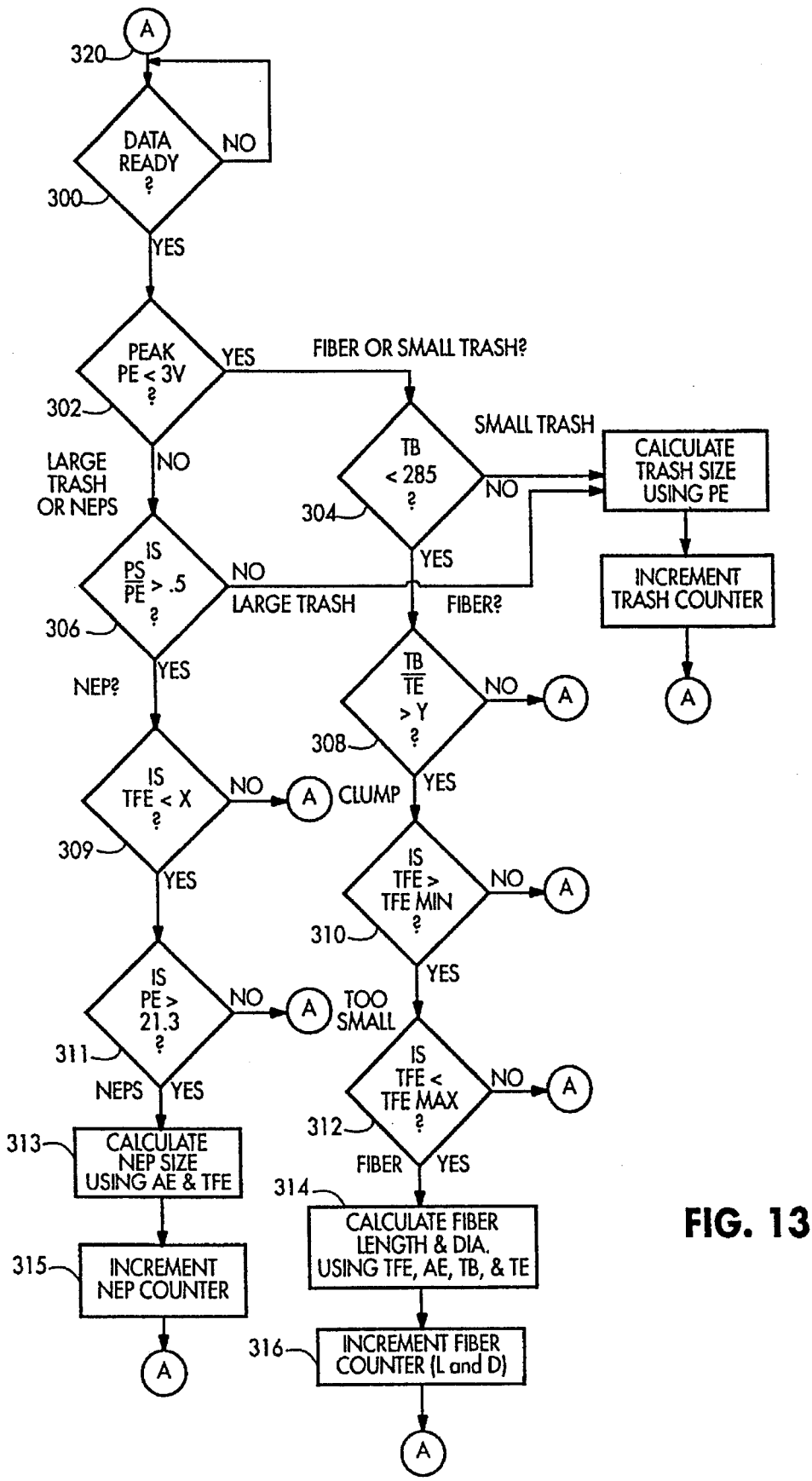
FIG. 13 is a flowchart illustrating how the computer acquires and analyzes data and classifies neps, trash and fiber data.

FIG. 12 illustrates typical analog signals or waveforms on the signal lines 170, 180 and 190 created by a fiber, a nep and a trash particle. The data acquisition board measures each of the three signals and passes to the computer, via the PC backplane, the eight parameters shown in FIG. 12: TB, TE, TFE, TFS, PE, AE, AS and PS. These eight parameters are used to classify, count and size the three types of entities. This classification procedure is shown in flowchart form in FIG. 13, and the logical operation is as follows: The computer waits at block 300 for the DAB to signal that a pulse with peak amplitude greater than 0.5V has been received. The first test at block 302 determines if the peak value on the extinction channel, PE, is less than 3 volts or greater. If PE is less than 3 volts the program moves to block 304 having eliminated the possibility that the pulse was a nep. If PE is greater than 3 volts the pulse is either a trash particle or a nep and the software moves to block 306.

If PE was less than 3 volts in block 302 and TB is less than 285 in block 304, (i.e. 285 counts of the 20 MHz clock) a small trash pulse has been captured and the size of the trash particle is calculated from PE and the trash counter incremented. The size calibration is described in Application Ser. No. 07/762,905 now U.S. Pat. No. 5,321,496.

If PE was less 3 volts in block 302 and TB is greater than 285 in block 304, the software has eliminated the possibility of a nep or trash particle and begins a set of tests to determine if the pulse is an acceptable fiber pulse in blocks 308, 310 and 312. If all 3 of the tests pass, the program calculates fiber length using TFE, TB and TE, calculates diameter using AE and TFE and increments the fiber counter in blocks 314 and 316. For staple textile fibers, we have discovered these preferable values: TB/TE >4=1.05 (value derived for each sensor during calibration); TFE min=100 and TFE max=10,000. (Values are counts of 10 MHz clock).

If PE was greater than 3 volts in block 302 and the ratio of PS to PE is less than 0.5 in block 306, a large trash pulse has been acquired. The size of the trash particle is calculated and the trash counter incremental as before.

If PE was greater than 3 volts in block 302 and the ratio of PS to PE is greater than 0.5, the software has eliminated the possibility of a fiber or a trash particle. The software tests the pulse in block 309 and block 311 to reject large clumps and small multiple fiber entanglements. A typical value for TFE<X is 300. If both tests and satisfied, a nep has been identified and its size is calculated from AE and TFE 313 and the nep counter 315 is incremented. Program control returns to the start block A 320 after each entity is identified.

Figure 14:
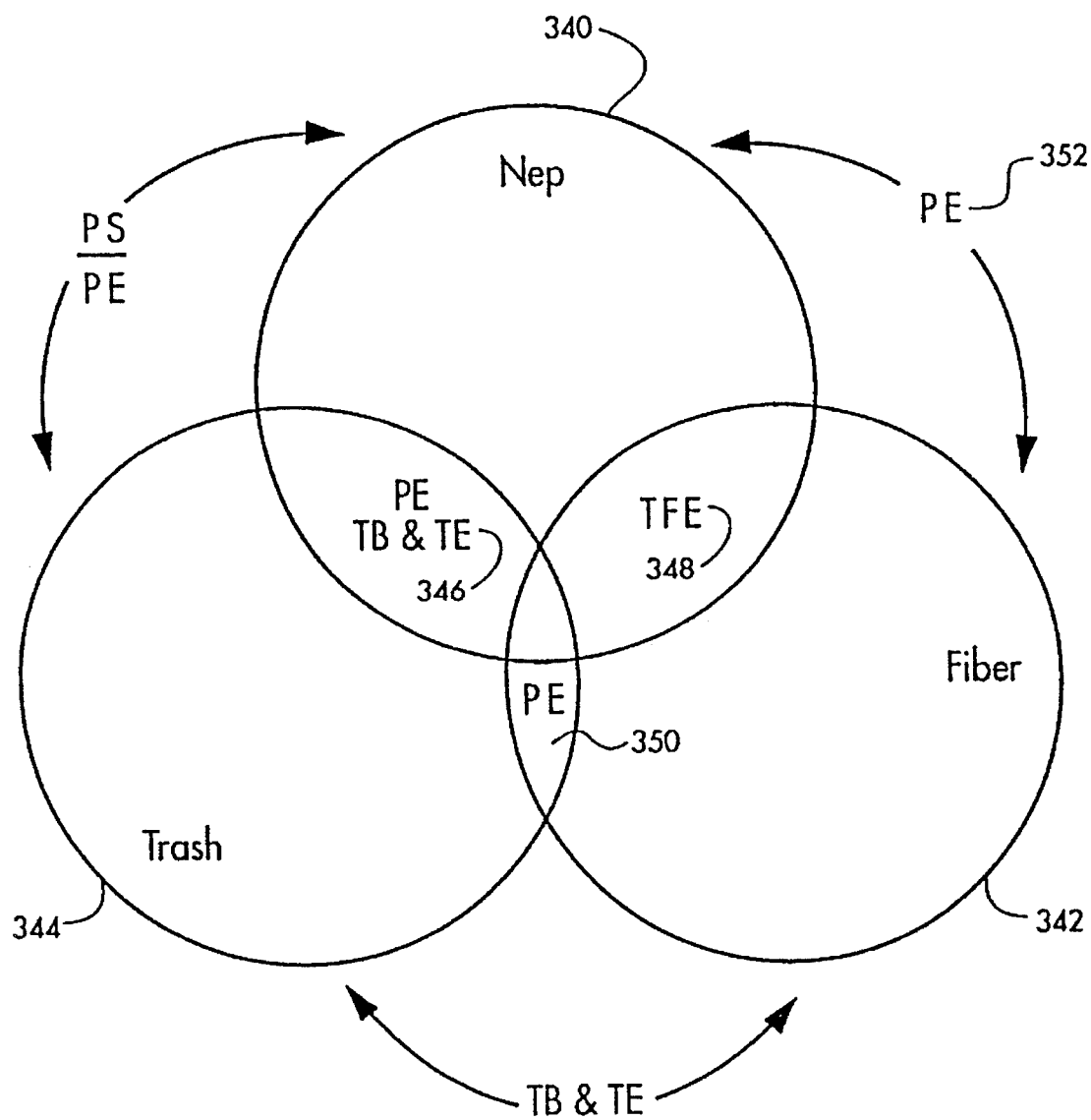
FIG. 14 is a Venn diagram showing the inter-relationship among the entity electro-optical parameters.

The relationship of the data from the DAB to the three entity types is shown in the Venn Diagram of FIG. 14. The three circles 340, 342 and 344 represent nep characteristics, trash particle characteristics and fiber characteristics. Characteristics that are common such as PE, TB and TE for nep 340 and trash 344 are inside the region of intersection 346. Characteristics that distinguish particles are shown outside the 3 circles 340, 342 and 344. An example would be parameter PE 352 for nep parameters 340 and fiber parameters 342. Using these parameter relationships, the flowchart, FIG. 13, was derived.

With the operation of the sensor(s) 82, data acquisition board(s) 161-G, and computer 18 in mind, one may now appreciate the different advantages of the embodiments represented by FIGS. 8 and 9.

The embodiment represented by FIG. 8 is a compromise between the embodiments of FIGS. 7 and 9. In the embodiment of FIG. 8, the trash is separated and stored for a period of time and then it is separately passed through the sensor 82. This embodiment offers the advantage of only one sensor and the analysis of the data is easier because the program will know when it is receiving trash. However, the time for a sample to be tested is increased somewhat because the trash is tested only after all of the fibers and neps have been tested. The primary advantage offered by the embodiment of FIG. 8 is that the analysis of the data is made easier.

If the embodiment of FIG. 9 is used, the program in computer 18 will know that the trash sensor 82a (and DAB therewith connected) only contains data corresponding to trash. This is so because the trash is physically separated from fibers and neps and the trash is placed through a separate sensor 82a.

Likewise, since no trash is in conduit 102 in the embodiment shown in FIG. 9, the program will know that fiber and nep data only appear on the data acquisition board connected to sensor 82. Because neps are always very large compared to fibers, the fiber—nep classification is easy. Thus, while the embodiment represented by FIG. 9 requires more sensors and may be more expensive and complex from a mechanical physical viewpoint, it reduces the complexity of the analysis and speeds the operation.

While several embodiments of the invention have been described in the foregoing Detailed Description, it will be understood that the invention is capable of numerous rearrangements, modifications and substitutions of parts without departing from the scope of the invention as defined by the appended claims.

We claim:

1. A textile testing apparatus for measuring characteristics of entities in a sample of textile material including entities of fiber, neps and trash, comprising:

a receiver for receiving a plurality of samples of textile material, said receiver including a plurality of sample receptacles, each of said sample receptacles being configured for releasably receiving one of said samples of textile material, said receptacles being positioned on said receiver so that the samples are held separate from one another by the sample receptacles, said receiver including a receiver output and being operable to position each of said samples for being fed one at a time out of said receiver;

an automatic feed mechanism disposed adjacent said receiver output and including a transportation path and a feed output, said automatic feed mechanism being positionable relative to said receiver for selectively engaging said samples in said sample receptacles of said receiver one at a time at said receiver output, removing said samples from said receiver one at a time, and transporting said samples along said transportation path to said feed output one at a time;

a textile processor having a processor input and a processor output, said processor input for receiving said sample from said feed output, said processor being operable for processing said sample, releasing the entities, including fibers, trash and neps, one from the other, individualizing said entities of the sample, and producing entities to the processor output in an individualized condition;

sensor means;

transport means for transporting individual ones of said entities to said sensor means;

said sensor means being operable to sense at least one characteristic of said individualized ones of said entities; and control means for detecting the presence or absence of a sample and for selectively actuating said automatic feed mechanism to engage and transport a sample from said receiver to said processor partly in response to the detection of the absence of a sample.

2. The apparatus of claim 1 wherein said receiver comprises:

a magazine for holding a plurality of fiber samples;

a plurality of elongate receptacles formed in said magazine and being disposed in the side by side relationship;

indexing means for supporting and moving said magazine for positioning a selected one of said elongated receptacles adjacent said output and automatic feed mechanism, for feeding the textile sample held in the selected said receptacle to said automatic feed mechanism; and said control means being operable to selectively actuate said indexing means to move and index a selected one of said elongate receptacle into a position adjacent said automatic feed mechanism.

3. The apparatus of claim 1 further comprising:

an optical sensor for sensing the presence or absence of a textile sample in said automatic feed mechanism and producing a sample detect signal; and said control means being responsive to the sample detect signal to selectively actuate said feed mechanism based in part on the presence or absence of a sample detect signal.

4. The apparatus of claim 1 wherein said automatic feed mechanism comprises:

a feed belt;

a feed belt motor for driving the feed belt;

a feed belt mount for supporting and moving said belt towards and away from said output of said receiver for selectively engaging said feed belt with a sample in said receiver output; and said control means being operable to selectively actuate said feed belt mount to move said feed belt into engagement with a sample in said receiver output to remove said sample and transport said sample to said feed output.

5. An apparatus for measuring characteristics of entities in a sample of textile material, including fiber, trash and neps, comprising:

supply means for supplying a sample of textile material;

processor means including a processor input and a processor output, said processor input being positioned and operable to receive the textile sample from said supply means, said processor means being operable for processing said sample, releasing the entities of said sample one from the others, individualizing the entities of the sample to produce single entities, and producing entities at said processor output in an individualized condition;

sensor means for substantially simultaneously sensing a plurality of characteristics of a sample;

transport means for transporting individualized ones of said entities to said sensor means, said transport means including a single airstream for transporting and presenting individualized fibers, neps and trash in a random order to said sensor means;

said sensor means being operable to sense at least one characteristic of a portion of the fibers, a portion of the neps and a portion of the trash from each single sample of textile material as said fibers, neps and trash are randomly presented at said sensor means and for producing characteristic signals corresponding to said sensed characteristics to provide substantially simultaneous measurement of multiple data from the same sample of material;

analysis means for receiving said characteristic signals, analyzing said characteristic signals to identify segments of said characteristic signals that correspond to one of said fibers, trash or neps, and further analyzing said segments to distinguish and identify each segment as corresponding to one of either a fiber, a trash particle, or a nep, whereby said analysis means identifies at least a portion of the randomly presented fibers, neps and trash as being either fiber, nep or trash.

6. The apparatus of claim 5 wherein said analysis means further comprises sub-analysis for determining whether a signal segment corresponds to a nep and, if so, producing a nep data acquisition command; and memory means for deriving and storing nep data from a particular signal segment in response to said nep data acquisition command.

7. The apparatus of claim 5 wherein said analyzing means comprises:

sub-analyzing means for first determining whether a signal segment corresponds to a nep and, if so, producing a nep data acquisition command, and secondly for determining whether a signal segment corresponds to a piece of trash and, if so, producing a trash data acquisition command; and means for deriving and storing nep data from a particular signal segment in response to said nep data acquisition command and for deriving and storing trash data from a particular signal segment in response to said trash data acquisition signal.

8. The apparatus of claim 5 wherein said analysis means comprises:

sub-analysis means for first determining whether a signal segment corresponds to a nep and, if so, producing a nep data acquisition command, and secondly for determining whether a signal segment corresponds to a piece of trash and, if so, producing a trash data acquisition command, and, thirdly, for determining whether a signal segment corresponds to a fiber and, if so, producing a fiber data acquisition command; and memory means for deriving and storing data in response to said nep data acquisition command, trash data acquisition command and fiber data acquisition command.

9. The apparatus of claim 5, wherein said sensor means comprises:

a light source for producing and directing light to impinge upon entities to be sensed in said sensor means;

an extinction sensor for sensing light and producing an output corresponding to the light extinction caused by an entity in said sensor and for producing an extinction signal corresponding to said light extinction; and a forward scatter sensor for sensing light scattered forward by an entity in the sensor and for producing a forward scatter signal corresponding to the forward scattered light from the entity; and wherein said analysis means further comprises sub-analysis means for comparing said light extinction signal to said forward scatter signal and, based in part on said comparison, determining whether a particular signal segment corresponds to a nep or trash.

10. The apparatus of claim 5:

wherein said sensor means comprises a light source producing and directing light to impinge on entities to be sensed in said sensor means; and an optical sensor for sensing entities in said sensor and producing an optical signal when an entity is sensed; and wherein said analysis means further comprises sub-analysis means for comparing the amplitude of the optical signal to a threshold to determine whether a particular signal segment corresponds to a fiber or to a nep or trash based at least in part on said comparison.

11. The apparatus of claim 5 wherein said sensor means comprises:

a light source for producing and directing light to impinge entities in said sensor means; and an optical sensor for detecting disturbances in the light caused by the entities in said sensor and producing optical signals;

and wherein said analyzing means determines a ratio of two of said optical signals by comparing the amplitude of said optical signals to a selected threshold, compares said ratio to a ratio threshold, and based at least in part on said comparison determines whether a particular signal segment corresponds to a fiber or to a nep or trash.

12. The apparatus of claim 5 wherein said sensor means further comprises:
- an air transport including an airstream for transporting entities including fibers, neps and trash through said sensor means; and
- a speed sensor for determining the speed of entities as they are carried through said sensor means in the airstream and for producing a speed signal corresponding to the speed of the entity; and
- wherein said analyzing means further comprises a sub-analyzing means for comparing the speed signal to a speed threshold and, based in part on said comparison, determining whether a particular segment corresponds to a fiber or to a nep or trash.

13. An apparatus for measuring characteristics of entities in a sample of textile material including fibers, trash and neps, comprising:
- supply means for supplying a sample of textile material;
- processor means including a processor input and a processor output, said processor input being positioned and operable to receive the sample of textile material from said supply means, said processor means being operable for processing a sample, releasing the entities including fibers, trash and neps, one from the others, individualizing said entities to produce single entities, and producing entities at said processor output in an individualized condition;
- sensor means for sensing characteristics of said entities;
- transporting means including an airstream for transporting the entities from the processor means in the airstream to and through said sensor means;
- said sensor means including:
  - a sensor transport including an airstream for carrying the entities through said sensor;
  - a light source for producing and directing light onto entities in said sensor means in said airstream;
  - a first extinction sensor disposed within the sensor to the side of said sensor airstream for sensing light disturbances caused by said entities in said sensor means and producing a first extinction signal corresponding to the light extinction caused by said entities within said sensor;
  - a second extinction sensor positioned to the side of said sensor airstream in said sensor means, adjacent to said first extinction sensor, and being downstream from said first extinction signal sensor relative to said airstream, said second extinction sensor for sensing light disturbances caused by entities in said sensor and producing a second extinction signal corresponding to the light extinction caused by said entity in said sensor means;
  - a forward scatter light sensor disposed to the side of said airstream for sensing light scattered forward from said entities in the airstream in the sensor means and for producing a forward scatter signal corresponding to said forward scattered light;
  - analysis means for receiving said first and second extinction signals and said forward scatter signals as characteristic signals, analyzing said characteristic signals to identify segments of said characteristic signals that correspond to one of said fibers, trash or neps;
- said analyzing means being operable:
  - to compare a selected one of said first extinction signal, second extinction signals or forward scatter signal to a predetermined threshold;
  - if said selected one of said signals exceeds the threshold, to compare one of said first or second extinction signals to the forward scatter signal;
  - to produce a nep detect signal when the selected one signal exceeds the threshold and the ratio of the forward scatter signal to one of the extinction signals exceeds a predetermined ratio; and
  - to produce a trash detect signal when the selected one extinction signal exceeds the threshold and the ratio of the forward scatter signal to said one of the extinction signals does not exceed the predetermined ratio;
  - if said selected one of said extinction signals does not exceed the threshold, to compare the amplitude of said one of said extinction signals to the duration of said one of said extinction signals and based in part on such comparison to determine whether said entity is a fiber or trash.

14. An apparatus for measuring characteristics of entities in a sample of textile material including fibers, trash and neps, comprising:
- supply means for supplying a sample of textile material;
- processor means including a processor input and a processor output, said processor input being positioned and operable to receive the sample of textile material from said supply means, said processor means being operable for processing a sample, releasing the entities including fibers, trash and neps, one from the others, individualizing said entities to produce single entities, and producing entities at said processor output in an individualized condition;
- sensor means for sensing characteristics of said entities;
- transporting means including an airstream for transporting the entities from the processor means in the airstream to and through said sensor means;
- said sensor means including:
  - a sensor transport including an airstream for carrying the entities through said sensor;
  - a light source for producing and directing light onto entities in said sensor means in said airstream;
  - a first extinction sensor disposed within the sensor to the side of said sensor airstream for sensing light disturbances caused by said entities in said sensor means and producing a first extinction signal corresponding to the light extinction caused by said entities within said sensor;
  - a second extinction sensor positioned to the side of the sensor airstream in said sensor means, adjacent to said first extinction sensor, and being downstream from said first extinction signal sensor relative to said airstream, said second extinction sensor for sensing light disturbances caused by entities in said sensor and producing a second extinction signal corresponding to the light extinction caused by said entity in said sensor means;
  - a forward scatter light sensor disposed to the side of said airstream for sensing light scattered forward from said entities in the airstream in the sensor means and for producing a forward scatter signal corresponding to said forward scattered light;
  - analysis means for receiving said first and second extinction signals and said forward scatter signals as characteristic signals, analyzing said characteristic signals to identify segments of said characteristic signals that correspond to one of said fibers, trash or neps;
- said analyzing means being operable:

to compare a selected one of said first and second extinction signals or said forward scatter signal to a predetermined threshold, and if said selected one of said signals exceeds the threshold, to compare one of said first or second extinction signals to the forward scatter signal;

to produce a nep detect signal when the selected one signal exceeds the threshold and the ratio of the forward scatter signal to one of the extinction signals exceeds a predetermined ratio; and to produce a trash detect signal when the selected one extinction signal exceeds the threshold and the ratio of the forward scatter signal to one of the extinction signals does not exceed the predetermined ratio;

if said selected one of said extinction signals does not exceed the threshold, to determine the speed of said entity from said first and second extinction signals and based on said speed determine whether entity is a fiber or trash.

* * * * *